(12) United States Patent
Broell et al.

(10) Patent No.: US 8,084,640 B2
(45) Date of Patent: Dec. 27, 2011

(54) METHOD FOR THE CONTINUOUS PRODUCTION OF UNSATURATED CARBOXYLIC ACID ANHYDRIDES

(75) Inventors: Dirk Broell, Langen (DE); Hermann Siegert, Seeheim-Jugenheim (DE)

(73) Assignee: EVONIK ROEHM GmbH, Darmstadt (DE)

( * ) Notice: Subject to any disclaimer, the term of this patent is extended or adjusted under 35 U.S.C. 154(b) by 460 days.

(21) Appl. No.: 12/299,217

(22) PCT Filed: Mar. 14, 2007

(86) PCT No.: PCT/EP2007/052398
§ 371 (c)(1),
(2), (4) Date: Oct. 31, 2008

(87) PCT Pub. No.: WO2007/147652
PCT Pub. Date: Dec. 27, 2007

(65) Prior Publication Data
US 2009/0264673 A1    Oct. 22, 2009

(30) Foreign Application Priority Data
Jun. 23, 2006 (DE) .......................... 10 2006 029 320

(51) Int. Cl.
*C07C 65/00* (2006.01)
(52) U.S. Cl. ...................................... 562/888
(58) Field of Classification Search .................. None
See application file for complete search history.

(56) References Cited

U.S. PATENT DOCUMENTS

| | | | |
|---|---|---|---|
| 4,110,372 A * | 8/1978 | Hey et al. ................ | 562/606 |
| 4,857,239 A | 8/1989 | Hurtel et al. | |
| 6,743,407 B2 | 6/2004 | Schaefer et al. | |
| 6,977,310 B2 | 12/2005 | Ackermann et al. | |
| 6,979,432 B2 | 12/2005 | Schaefer et al. | |
| 7,288,402 B2 | 10/2007 | Osswald et al. | |
| 7,491,521 B2 | 2/2009 | Osswald et al. | |
| 2003/0018217 A1 * | 1/2003 | Dupont et al. ............. | 562/888 |
| 2006/0211880 A1 | 9/2006 | Ackermann et al. | |
| 2008/0194862 A1 | 8/2008 | Ackermann et al. | |

(Continued)

FOREIGN PATENT DOCUMENTS
DE        3510035    * 10/1986
(Continued)

OTHER PUBLICATIONS

U.S. Appl. No. 12/298,034, filed Oct. 22, 2008, May et al.

(Continued)

*Primary Examiner* — Karl J Puttlitz
(74) *Attorney, Agent, or Firm* — Oblon, Spivak, McClelland, Maier & Neustadt, L.L.P.

(57) ABSTRACT

Process for continuously preparing unsaturated carboxylic anhydrides of the general formula I

R—C(O)—O—C(O)—R    (I)

Figure 1:
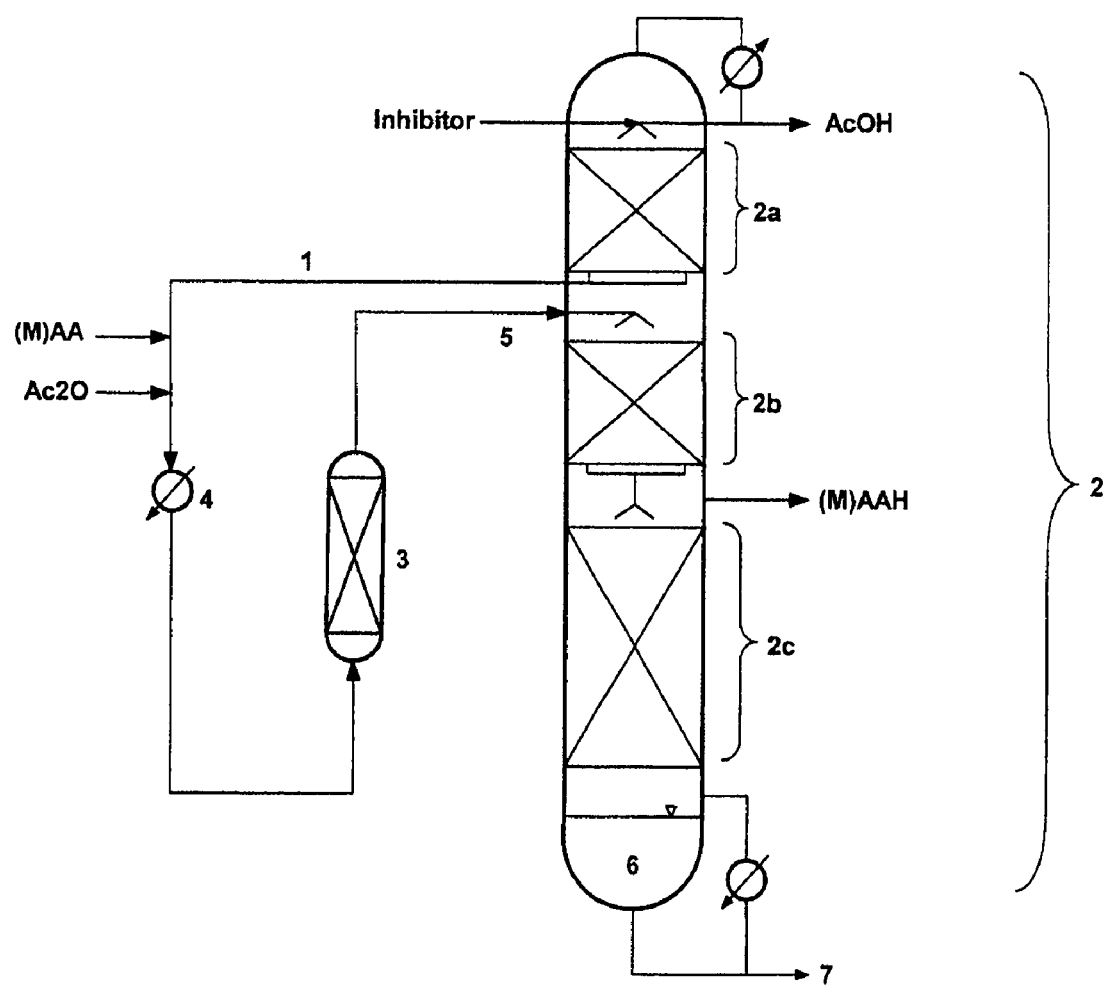

in which R is an unsaturated organic radical having 2 to 12 carbon atoms
by transanhydridization of an aliphatic carboxylic anhydride with a carboxylic acid of the general formula II

R—COOH    (II)

in which R is as defined above
in a rectification column having an upper, middle and lower region, characterized in that
f) an inert boiling oil is initially charged in the bottom of the column,
g) the reactants are fed into a reaction region in stoichiometric ratios,
h) the carboxylic acid formed as the by-product is withdrawn at the top of the column,
i) the unconverted reactants are recycled into the reaction region and
j) the product of the formula I is obtained via a side draw, preferably between the middle and lower column region.

10 Claims, 1 Drawing Sheet

U.S. PATENT DOCUMENTS

| | | |
|---|---|---|
| 2008/0194875 A1 | 8/2008 | Ackermann et al. |
| 2008/0248538 A1 | 10/2008 | Osswald et al. |
| 2008/0269431 A1 | 10/2008 | Sarcinelli et al. |
| 2009/0118533 A1 | 5/2009 | Broell et al. |

FOREIGN PATENT DOCUMENTS

| | | |
|---|---|---|
| EP | 0 004 641 | 10/1979 |
| EP | 0 196 520 | 10/1986 |
| FR | 2 877 003 | 4/2006 |

OTHER PUBLICATIONS

U.S. Appl. No. 12/300,189, filed Nov. 10, 2008, Broell et al.
U.S. Appl. No. 12/307,773, filed Jan. 7, 2009, Ackermann et al.
U.S. Appl. No. 12/441,145, filed Mar. 13, 2009, May et al.
U.S. Appl. No. 12/515,036, filed May 15, 2009, May et al.
U.S. Appl. No. 12/443,784, filed Mar. 31, 2009, Vogel et al.
U.S. Appl. No. 12/442,415, filed Mar. 23, 2009, Vogel et al.
U.S. Appl. No. 12/303,161, filed Dec. 2, 2008, Marx et al.
U.S. Appl. No. 12/517,563, filed Jun. 4, 2009, Broell.

* cited by examiner

METHOD FOR THE CONTINUOUS PRODUCTION OF UNSATURATED CARBOXYLIC ACID ANHYDRIDES

The invention relates to a process for continuously preparing unsaturated carboxylic anhydrides, in particular the reaction of an unsaturated carboxylic acid with a low molecular weight aliphatic carboxylic anhydride.

DE-A-3510035 describes a process for continuously preparing unsaturated carboxylic anhydrides by acid-catalysed transanhydridization reaction of acetic anhydride with an unsaturated carboxylic acid in the middle part of a distillation column. To achieve complete conversion, acetic anhydride is used in an excess of 0.1 to 0.5 mol per mole of carboxylic acid, in which case a mixture of acetic acid and acetic anhydride is obtained at the top of the column, i.e. pure acetic acid is not obtained.

In addition, the product is formed contaminated by the catalyst, which then has to be removed in a further process step.

U.S. Pat. No. 4,857,239 describes a process for preparing methacrylic anhydride, wherein the molar ratio of methacrylic acid to acetic anhydride is 2.1 to 3 and a polymerization inhibitor is added into the distillation column. According to the examples, the process is batchwise. An additional disadvantage is that the reactant used in excess is obtained unused.

US-A-2003/001827 describes a batchwise process for preparing methacrylic anhydride, wherein the initial molar ratio of methacrylic acid to acetic anhydride is preferably 9 to 11. The acetic acid formed is removed immediately and the reactor contents released are diluted with acetic anhydride. To prevent polymerization, inhibitors are added into the reactor and into the column. A large number of by-products are formed, and cannot be removed completely.

It is thus an object of the invention to provide an improved process for continuously preparing unsaturated carboxylic anhydrides, in which a stoichiometric excess of one of the reactants is avoided, but complete conversion of the reactants is nevertheless achieved, and, at the same time, the unsaturated anhydride and the carboxylic acid formed are obtained in high purity. In addition, polymerization should be largely prevented in all regions and the space-time yield of the reaction should be increased.

The invention provides a process for continuously preparing unsaturated carboxylic anhydrides of the general formula I $$R-C(O)-O-C(O)-R \qquad (I)$$

in which R is an unsaturated organic radical having 2 to 12 carbon atoms
by transanhydridization of an aliphatic carboxylic anhydride with a carboxylic acid of the general formula II $$R-COOH \qquad (II)$$

in which R is as defined above
in a rectification column having an upper, middle and lower region, characterized in that
a) an inert boiling oil is initially charged in the bottom of the column,
b) the reactants are fed into a reaction region in stoichiometric ratios,
c) the carboxylic acid formed as the by-product is withdrawn at the top of the column,
d) the unconverted reactants are recycled into the reaction region and
e) the product of the formula I is obtained via a side draw, preferably between the middle and lower column region.

These technical features achieve complete conversion of the reactants and simultaneously a high purity of the products, and substantial prevention of polymerization in all regions, since, among other reasons, long residence times of the unsaturated anhydride formed in the column bottom are ruled out.

Carboxylic acids suitable for the process according to the invention have an unsaturated organic radical having 2 to 12, preferably 2 to 6, more preferably 2 to 4 carbon atoms. Suitable alkenyl groups are the vinyl, allyl, 2-methyl-2-propenyl, 2-butenyl, 2-pentenyl, 2-decenyl, 1-undecenyl and the 9,12-octadecadienyl group. Particular preference is given to the vinyl group and the allyl group.

The particularly preferred carboxylic acids include (meth)acrylic acids. The term (meth)acrylic acids is known in the technical field, and is understood to refer to not only acrylic acid and methacrylic acid but also derivatives of these acids. These derivatives include β-methylacrylic acid (butenoic acid, crotonic acid), α,β-dimethylacrylic acid, β-ethylacrylic acid, α-chloroacrylic acid, α-cyanoacrylic acid, 1-(trifluoromethyl)acrylic acid and β,β-dimethylacrylic acid. Preference is give to acrylic acid (propenoic acid) and methacrylic acid (2-methylpropenoic acid).

Suitable carboxylic anhydrides for the process according to the invention are likewise known in the technical field. Preferred compounds have the general formula III R'—C(O)—O—C(O)—R' (III) in which R' is a $C_1$- to $C_4$-alkyl radical. Preference is given to using acetic anhydride.

For the process according to the invention, the boiling oil used is a high-boiling inert substance which is thermally stable over a long period and has a boiling point higher than the boiling points of the components involved in the reaction, in order to ensure the distillative removal of the acid anhydride formed without polymerization. The boiling point of the boiling oil should, though, not be too high either, in order to reduce the thermal stress on the acid anhydride formed.

In general, the boiling temperature of the boiling oil at standard pressure (1013 mbar) is from 200 to 400° C., especially from 240 to 290° C.

Suitable boiling oils include relatively long-chain unbranched paraffins having 12 to 20 carbon atoms, aromatic compounds such as Diphyl (eutectic mixture of 75% biphenyl oxide and 25% biphenyl), alkyl-substituted phenols or naphthalene compounds, sulpholane (tetra-hydrothiophene 1,1-dioxide) or mixtures thereof.

Suitable examples are the boiling oils shown below:

n-paraffin c14

75% biphenyl oxide + 25% biphenyl = Diphyl

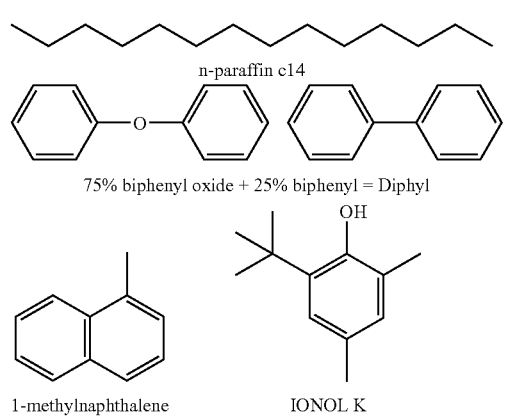

1-methylnaphthalene          IONOL K

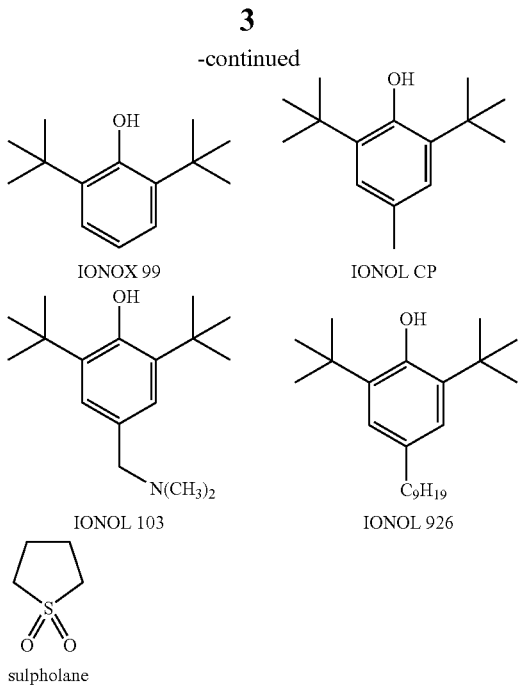

sulpholane

Particular preference is given to using 2,6-di-tert-butyl-para-cresol, 2,6-di-tert-butylphenol, sulpholane, Diphyl or mixtures thereof, very particular preference to sulpholane.

According to the invention, a stoichiometric ratio is understood to mean a molar ratio of 1.9 to 2.1:1 of carboxylic acid to carboxylic anhydride.

For the transanhydridization reaction according to the present invention, any rectification column which has 5 to 15 separating stages each in the upper, middle and lower region can be used. The number of separating stages is preferably 10 to 15 in the upper region and 8 to 13 in the middle and lower region. In the present invention, the number of separating stages refers to the number of trays in a tray column multiplied by the tray efficiency, or the number of theoretical plates in the case of a column with structured packing or a column with random packing.

Examples of rectification columns with trays include those such as bubble-cap trays, sieve trays, tunnel-cap trays, valve trays, slotted trays, slotted sieve trays, bubble-cap sieve trays, jet trays, centrifugal trays; for a rechfication column with random packings, those such as Raschig rings, Lessing rings, Pall rings, Berl saddles, Intalox saddles; and, for a rectification column with structured packings, those such as Mellapak (Sulzer), Rombopak (Kühni), Montz-Pak (Montz) and structured packings with catalyst pockets, for example Katapak (Sulzer).

A rectification column with combinations of regions of trays, of regions of random packings and/or of regions of structured packings may likewise be used.

Preference is given to using a rectification column with random packings and/or structured packings for the 3 regions.

The rectification column may be manufactured from any material suitable for this purpose. This includes stainless steel and inert materials.

The apparatus has at least one region, referred to hereinafter as reaction region or reactor, in which at least one catalyst is preferably provided. This reactor may be within and/or outside the rectification column. However, this reactor is preferably arranged outside the rectification column in a separate region, one of these preferred embodiments being illustrated in detail in FIG. 1.

The reaction is performed preferably at temperatures in the range of 30 to 120° C., more preferably at 40 to 100° C., in particular at 50 to 80° C. The reaction temperature depends on the system pressure established. In the case of an arrangement of the reactor within the column, the reaction is performed preferably in the pressure range of 5 to 100 mbar (absolute), in particular at 10 to 50 mbar (absolute) and more preferably at 20 to 40 mbar (absolute).

If the reactor is outside the column, different pressure and temperature conditions can be selected there from those in the column. This has the advantage that the reaction parameters of the reactor can be set independently of the operating conditions in the column.

The reaction time of the transanhydridization depends on the reaction temperature; the residence time in the reactor in single pass is preferably 0.5 to 15 minutes and more preferably 1 to 5 minutes.

In the preparation of (meth)acrylic anhydride from acetic anhydride and (meth)acrylic acid, the reaction temperature is preferably 40 to 100° C., more preferably 50 to 90° C. and most preferably 70 to 85° C.

In addition to the reactants, the reaction mixture may comprise further constituents, for example solvents, catalysts and polymerization inhibitors.

Preference is given to using heterogeneous catalysts in the reaction region. Particularly suitable heterogeneous catalysts are acidic fixed bed catalysts, especially acidic ion exchangers.

The particularly suitable acidic ion exchangers include, in particular, cation exchange resins such as sulphonic acid-containing styrene-divinylbenzene polymers. Suitable cation exchange resins can be obtained commercially from Rohm & Haas under the trade name Amberlyst®, from Dow under the trade name Dowex® and from Lanxess under the trade name Lewatit®.

The amount of catalyst in 1 is preferably $\frac{1}{10}$ up to 2 times, more preferably $\frac{1}{5}$ to $\frac{1}{2}$ times, the amount of newly formed unsaturated carboxylic anhydride to be produced in 1/h.

The polymerization inhibitors usable with preference include octadecyl 3-(3,5-di-tert-butyl-4-hydroxy-phenyl) propionate, phenothiazine, hydroquinone, hydroquinone monomethyl ether, 4-hydroxy-2,2,6,6-tetra-methylpiperidinooxyl (TEMPOL), 2,4-dimethyl-6-tert-butylphenol, 2,6-di-tert-butylphenol, 2,6-di-tert-butyl-4-methylphenol, para-substituted phenylene-diamines, for example N,N'-diphenyl-p-phenylenediamine, 1,4-benzoquinone, 2,6-di-tert-butyl-alpha-(dimethyl-amino)-p-cresol, 2,5-di-tert-butylhydroquinone, or mixtures of two or more of these stabilizers. Very particular preference is given to phenothiazine.

The inhibitor can be metered into the feed upstream of the reactor and/or into the rectification column, preferably at the top thereof.

According to the invention, the transanhydridization is effected in an apparatus, wherein the feed streams of the reactants are introduced into the reaction region of the rectification column with the reactor circulation stream which predominantly of unconverted reactants and an intermediate of the formula R—C(O)—O—C(O)—R' where R and R' are each as defined above. The abovementioned inert boiling oil is present in the bottom of the column, in order to prevent long residence times of the target product which is prone to polymerization. The unsaturated carboxylic anhydride as the target product is drawn off preferably in gaseous form between the middle and lower region, while the newly formed carboxylic acid is drawn off at the top of the column as the lowest-boiling reaction component.

Unconverted reactants and intermediates formed are recycled into the reaction region, for example by means of a pump.

High boilers such as added inhibitors can be discharged from the bottom by customary methods, for example by means of a thin-film evaporator or an apparatus which performs similar functions, the substances to be evaporated are recycled into the rectification column and non-evaporating high boilers are discharged.

If a catalyst is used, it can be provided in each region of the rectification column, preferably in the middle region.

In addition, the catalyst may be provided in a separate region of the apparatus, the reaction region or reactor, this region being connected to the further regions of the apparatus. This separate arrangement of the catalyst region is preferred, and the reactants can be passed constantly through the catalyst region. This continuously forms the unsaturated carboxylic anhydride, for example (meth)acrylic anhydride, and the newly formed carboxylic acid, for example acetic acid.

A preferred embodiment of the process according to the invention is shown schematically in FIG. 1.

The feed streams of (meth)acrylic acid (=(M)AA) and acetic anhydride (=$Ac_2O$) are fed to a reactor (3) positioned outside the rectification column (2) with the circulation stream (1) which consists predominantly of unconverted reactants and the acetyl (meth)acrylate intermediate formed.

The temperature of the reactants can be adjusted by means of a heat exchanger (4) in the feed.

The reactor is preferably a flow tube reactor which comprises a fixed bed catalyst.

The reactor exit stream (5) is fed into the rectification column (2), preferably below the reflux stream from the upper region (2a) of the column. In the column (2) firstly the further reaction and secondly the separation of the components take place. To prevent polymerization, inhibitor is preferably metered in at the top of the column.

In the upper region (2a), the low-boiling acetic acid is removed from the medium boilers (reactants, intermediate) and drawn off at the top. In the middle region (2b) of the column, the separation of medium boilers from (meth)acrylic anhydride (=(M)AAH) takes place, (M)AAH preferably being drawn off in gaseous form between the middle and lower part. In the lower region (2c) of the column, (M)AAH is separated from the boiling oil (6) present in the bottom. High boilers present in the bottom can be discharged by customary methods (7), for example by means of a thin-film evaporator or an apparatus which performs similar functions, the evaporating substances are recycled into the rectification column and non-evaporating high boilers are discharged.

The liquid stream resulting from the upper region (2a) is drawn off completely from the column and fed to the reactor as the circulation stream (1) together with the feed streams.

The present invention will be illustrated in detail hereinafter with reference to examples.

EXAMPLE 1

Preparation of Methacrylic Anhydride

For the preparation of methacrylic anhydride by reaction of methacrylic acid and acetic anhydride, a test plant according to FIG. 1 was set up. The rectification column (2) had a total of approx. 35 separating stages (15 in the upper region (2a), 12 in the middle region (2b) and 8 in the lower region (2c)). With connecting pieces and bottom, this column was 5.5 m high, had an internal diameter of 100 mm and was equipped with Sulzer CY packings (region 2a and 2b) and Montz BSH 400 packings (region 2c). The polymerization inhibitor used was phenothiazine. The pressure at the top of the column was 20 mbar. Under steady-state conditions, a temperature profile of 164° C. (bottom) to 23° C. (column top) was established. The discharges of acetic acid at the top of the column and methacrylic anhydride at the side draw (between region 2b and 2c) and the heating steam output of the bottom evaporator were controlled by setting suitable temperatures in the particular regions.

In the bottom of the rectification column, 6 kg of sulpholane were used as boiling oil (6). The evaporator used was a falling-film evaporator.

The reaction was performed in the external reactor (3). The heterogeneous solid-state catalyst used was 450 ml of the acidic ion exchanger Lewatit K2431 from Lanxess. The reaction temperature was 76° C. The circulation stream (1) coming from the column, approx. 16 kg/h, which consisted primarily of unconverted reactants and the acetyl methacrylate intermediate, passed back into the reactor with the fresh feed of methacrylic acid and acetic anhydride.

1750 g/h of acetic anhydride and 2951 g/h of methacrylic acid were metered in freshly and continuously.

At the top of the column, 2038 g/h of acetic acid were obtained. At the side stream draw, 2616 g/h of methacrylic anhydride were withdrawn with a purity of 99.7% (GC analysis). The yield of methacrylic anhydride based on acetic anhydride used and methacrylic acid used was 99%.

EXAMPLE 2

Preparation of Acrylic Anhydride

For the preparation of acrylic anhydride by reaction of acrylic acid and acetic anhydride, the same test plant as illustrated in Example 1 was used.

The pressure at the top of the column, the reaction temperature and the circulation stream were virtually identical to the values reported in Example 1. The same reactor arrangement, the same polymerization inhibitor, the same catalyst (type and amount) and the same boiling oil (type and amount) were likewise used. Under steady-state conditions, a temperature profile of 167° C. (bottom) to 23° C. (column top) was established.

1500 g/h of acetic anhydride and 2118 g/h of acrylic acid were metered in continuously and freshly.

At the top of the column, 1712 g/h of acetic acid were obtained. At the side stream draw, 1797 g/h of acrylic anhydride were withdrawn with a purity of 99.7% (GC analysis). The yield of acrylic anhydride based on acetic anhydride used and acrylic acid used was 97%.

The invention claimed is:

1. A continuous process for preparing an unsaturated carboxylic anhydride of formula (I):

R—C(O)—O—C(O)—R        (I)

wherein R is an unsaturated organic radical having 2 to 12 carbon atoms, comprising:
feeding a carboxylic acid of formula (II)

R—COOH        (II)

wherein R is as defined above,
and an aliphatic carboxylic anhydride to a reaction region containing a heterogeneous catalyst in a molar ratio of carboxylic acid to aliphatic carboxylic anhydride of 1.9/1 to 2.1/1;
transanhydridizing the aliphatic carboxylic anhydride with the carboxylic acid of formula (II) in the reaction region containing a heterogeneous solid-state catalyst; and separating the unsaturated carboxylic anhydride of Formula (I), a carboxylic acid obtained by hydrolysis of the aliphatic carboxylic anhydride and unconverted reactants in a rectification column having an upper, middle and lower region, wherein an inert boiling oil is initially charged in the bottom of the column, the carboxylic acid formed as a by-product is withdrawn at the top of the column, the unconverted reactants are recycled into the reaction region and the product of the formula I is obtained via a side draw, between the middle and lower column region.

2. The process according to claim 1, wherein the heterogeneous catalyst in the reaction region is a solid state catalyst.

3. The process according to claim 2, wherein the heterogeneous catalyst is an acidic fixed bed catalyst.

4. The process according to claim 2, wherein the heterogeneous catalyst is a cationic exchanger.

5. The process according to claim 1, wherein the reaction region is outside the rectification column.

6. The process according to claim 1, wherein the unsaturated carboxylic anhydride of formula I is (meth)acrylic anhydride, prepared by transanhydridization of acetic anhydride and (meth)acrylic acid.

7. The process according to claim 1, wherein the inert boiling oil has a boiling point higher than boiling points of the components involved in the reaction.

8. The process according to claim 1, wherein the inert boiling oil is at least one selected from the group consisting of 2,6-ditert-butyl-para-cresol, 2,6-di-tert-butylphenol, sulpholane and Diphyl.

9. The process according to claim 8, wherein the inert boiling oil is sulpholane.

10. The process according to claim 1, further comprising:
discharging high-boiling components from the column bottom and recycling evaporating substances into the reaction region.

* * * * *